(12) United States Patent
Schlumpberger

(10) Patent No.: US 9,097,628 B2
(45) Date of Patent: Aug. 4, 2015

(54) METHOD AND KIT FOR PROCESSING WAX-EMBEDDED BIOLOGICAL SAMPLES

(75) Inventor: Martin Schlumpberger, Hilden (DE)

(73) Assignee: QIAGEN, GMbH, Hilden ( * ) Notice: Subject to any disclaimer, the term of this patent is extended or adjusted under 35 U.S.C. 154(b) by 71 days.

(21) Appl. No.: 13/996,437

(22) PCT Filed: Dec. 23, 2011

(86) PCT No.: PCT/EP2011/073912
§ 371 (c)(1),
(2), (4) Date: Jun. 20, 2013

(87) PCT Pub. No.: WO2012/085261
PCT Pub. Date: Jun. 28, 2012

(65) Prior Publication Data
US 2013/0280728 A1    Oct. 24, 2013

(30) Foreign Application Priority Data
Dec. 23, 2010  (EP) .................................. 10016021

(51) Int. Cl.
*G01N 1/30* (2006.01)
*C12N 15/10* (2006.01)
(52) U.S. Cl.
CPC .............. *G01N 1/30* (2013.01); *C12N 15/1003* (2013.01)
(58) Field of Classification Search
None
See application file for complete search history.

(56) References Cited

U.S. PATENT DOCUMENTS

| 4,162,897 A * | 7/1979 | Capuano ....................... 436/106 |
| 5,552,087 A * | 9/1996 | Zeheb et al. ............... 252/408.1 |
| 2004/0072305 A1 | 4/2004 | Erlander et al. |
| 2007/0172911 A1 | 7/2007 | Farrell et al. |
| 2013/0095473 A1 * | 4/2013 | Groelz ........................... 435/6.1 |
| 2013/0164826 A1 * | 6/2013 | Zhou ............................ 435/270 |

FOREIGN PATENT DOCUMENTS

| EP | 2 071 313 A1 | 6/2009 |
| WO | 01/46402 A1 | 6/2001 |
| WO | 2009/127350 A1 | 10/2009 |
| WO | 2012/085261 A1 | 6/2012 |

OTHER PUBLICATIONS

Buesa, Rene J. et al., "Histology without xylene," *Annals of Diagnostic Pathology*, 13:246-256 (2009).
Ludwig, D. Brett et al., "Protein Adsorption and Excipient Effects on Kinetic Stability of Silicone Oil Emulsions," *Journal of Pharmaceutical Sciences*, 99(4):1721-1733 (2010).
Okello, John B.A. et al., "Comparison of methods in the recovery of nucleic acids from archival formalin-fixed paraffin-embedded autopsy tissues," *Analytical Biochemistry*, 400:110-117 (2010).
International Search Report for International Application No. PCT/EP2011/073912, mailed on Feb. 22, 2012.

* cited by examiner

*Primary Examiner* — Allison Fox
(74) *Attorney, Agent, or Firm* — Seed IP Law Group PLLC

(57) ABSTRACT

The present invention relates to a method for processing a wax-embedded biological sample, the use of poly(organosiloxane)s for liquefying the embedding medium of a wax-embedded biological sample and a kit for processing a wax-embedded biological sample.

38 Claims, No Drawings

METHOD AND KIT FOR PROCESSING WAX-EMBEDDED BIOLOGICAL SAMPLES

The present invention relates to a method for processing a wax-embedded biological sample, the use of poly(organosiloxane)s for liquefying the embedding medium of a wax-embedded biological sample and a kit for processing a wax-embedded biological sample.

On removal of biological material from a living organism, e.g. a tissue fragment or isolated cells, the cells mortify after a short time, unless usual measures are taken, such as, for instance, incubation in nutrient media. Mortified cells moreover rapidly undergo initial autolytic-fermentative and then bacterial decomposition, so that the original cell-in-tissue structures are destroyed. Thus, it is necessary to fix the removed biological sample in order to suppress its decomposition if a histological examination of the sample is envisaged. By means of fixation it is intended to substantially preserve the biological structures in a life-like fashion to allow a "real assessment". In addition, fixed specimens can be stored and archived for a long time. Furthermore, many morphological investigations are only possible on the basis of fixed material.

Fixation usually is achieved using precipitating or crosslinking compounds such as acids, alcohols, ketones, or aldehydes. For fixation in particular formaldehyde is employed (usually in the form of a 4-10 wt.-% aqueous solution, referred to as "formalin"), commonly followed by a step of embedding the fixed material in a wax, usually paraffin, resulting in a so-called "formalin-fixed, paraffin-embedded" (FFPE) material. The main purpose of the embedding medium is to permit the specimens to be sectioned and mounted in the natural state for microscopic and/or histochemical applications. For many applications it is however necessary or at least advantageous to remove the embedding medium prior to further processing of the sample, for instance for histological staining or isolating specific biomolecules, e.g. nucleic acids such as DNA and/or RNA, from a lysate obtainable after lysing the de-waxed sample.

Traditionally, deparaffinization involves the use of aromatic solvents such as toluene and, in particular, xylene. Typically, a fresh slice or a microscope slide mounted specimen is immersed in a xylene bath until the paraffin is solubilized. In subsequent steps the deparaffinized specimen is washed by a series of aqueous alcohol solutions of decreasing alcohol concentration to remove xylene prior to a final wash using water, to make the sample accessible for aqueous reactant or reagent solutions, such as for example lysis buffers or staining solutions. Xylene, however, is a flammable, volatile and toxic organic solvent.

For this reason, in recent years considerable efforts have been made to replace xylene with less toxic de-waxing agents. Examples for xylene replacements in histochemical applications include terpene oils, such as d-limonene, isoparaffinic hydrocarbons or aqueous dishwashing soap solutions (R. J. Buesa, M. V. Peshov, Annals of Diagnostic Pathology 2009, 13, 246-256). Several of these de-waxing agents perform equal to xylene with regard to wax removal while being less or even non-toxic. However, a series of alcohol washes in many cases is still required to remove the solvent/de-waxing agent prior to a water wash to achieve compatibility with most types of immunohistochemical stainings or aqueous lysis buffers.

In some methods known from the state of the art (see for example WO 2009/153299 A1 or the protocol to the PureLink™ FFPE Total RNA Isolation Kit provided by the manufacturer Invitrogen, Carlsbad, Calif., USA), the wax-embedded sample simply is heated in an aqueous solution to melt the wax and then centrifuged to separate the aqueous from the waxy phase. Upon re-solidifying of the waxy phase, the wax deposits as a layer above the aqueous solution and/or at the walls of the container/tube, from where it may be collected and thus separated from the biological sample. However, the re-solidified wax may interfere with further sample processing steps, e.g. by clogging pipet tips, which complicates automated sample handling.

With advances in biomolecular techniques, not only light microscopic inspection of wax-embedded samples, but also analysis of biomolecules, in particular of nucleic acids, both, DNA and RNA, recovered from wax-embedded samples became increasingly important. Nucleic acids recovered from such samples may subsequently be analyzed using highly sensitive techniques such as for example polymerase chain reaction (PCR). If, however, the extraction of nucleic acids from a wax-embedded sample is envisaged instead of or in addition to immunohistochemical staining, it is very important that the de-waxing agents either do not interfere in any subsequent step of concentrating, purifying, isolating and/or analyzing the nucleic acids or that said agents can be completely removed from the sample after de-waxing. For recovery of nucleic acids from FFPE samples, said samples are usually de-waxed using xylene and washed a number of times with aqueous alcohol solutions of decreasing alcohol concentration as described above, before being lysed in an appropriate digestion/lysis buffer. In subsequent steps nucleic acids are usually isolated from these buffers using organic extraction methods such as phenol/chloroform extraction and optionally further concentrated by precipitating using for example ethanol or isopropanol.

A further approach for de-waxing biological samples makes use of rather inert, non-polar mineral oil. While mineral oil has a boiling point well above 100° C. and a low volatility at temperatures in the range of about 80 to 100° C., a serious drawback in light of fast sample processing is its rather high kinematic viscosity. While the exact value of the kinematic viscosity depends upon the specific mineral oil employed, the kinematic viscosity of mineral oils employed for de-waxing usually is well above $10 \text{ mm}^2 \cdot \text{s}^{-1}$ (R. J. Buesa, M. V. Peshov, Annals of Diagnostic Pathology 2009, 13, 246-256), which complicates pipetting and further steps necessary for removing said solvent from the sample.

Thus, in co-pending application EP10 165 799.7, mineral oil has been replaced by linear alkanes, for example hexadecane. This approach even allows further processing of the biological sample in the presence of the liquefied embedding medium, e.g. lysing of cell structures using an aqueous lysing buffer. However, in linear alkanes a relationship exists between the boiling point and the kinematic viscosity of the alkane. The higher the boiling point of the alkane is, the higher is its kinematic viscosity. Using pure linear alkanes it is thus not possible to obtain a de-waxing agent which has a kinematic viscosity comparable to that of water ($1 \text{ mm}^2 \cdot \text{s}^{-1}$, equaling 1 cSt), but having a boiling point well above 100° C.

It was an object of the present invention to provide a rapid and automatable method for processing a wax-embedded biological sample which avoids the use of both, toxic de-waxing agents, like for example xylene, and laborious and time-consuming washing steps for removing the de-waxing agent from the sample. In particular, the method preferably should be compatible with both, standard pipetting automats in order to be automatable and heating steps of up to 95° C. in the presence of the de-waxing agent.

This object is met by the method of the present invention. In the present invention, it has surprisingly been found that poly(organosiloxane)s are particularly useful for de-waxing wax-embedded biological samples.

In terms of the present invention the term "de-waxing" refers to any sequence of steps comprising at least one step of liquefying and/or solubilizing the embedding medium of a wax-embedded biological sample and at least one step of separating the liquefied and/or solubilized embedding medium from at least a part of the biological sample. The steps of liquefying and/or solubilizing the embedding medium and separating the liquefied and/or solubilized embedding medium from at least a part of the biological sample may be carried out (almost) simultaneously or one after another. However, it may be particularly preferred that the biological sample is further processed in the presence of the liquefied and/or solubilized embedding medium, before said medium is finally removed from at least a part of the biological sample.

In terms of the present invention the term "removed from at least a part of the biological sample" is used to indicate that the embedding medium does not have to be removed completely from such parts of the biological sample which are of interest for further analysis. E.g. if a tissue section is processed according to the method of the present invention in order to prepare said section for histological staining, the liquefied and/or solubilized embedding medium usually will be removed from (essentially) the whole sample. If, on the other hand, only specific biomolecules of the sample are of interest for further analysis, such as for example nucleic acids or proteins, it is not mandatory to separate the liquefied and/or solubilized embedding medium from the whole biological sample, but only from these biomolecules of interest.

Poly(organosiloxane)s are efficient in liquefying and/or solubilizing the embedding medium of a wax-embedded biological sample at a broad temperature range without compromising the integrity of the biological material. Typically, the biological sample may be subjected to processing temperatures ranging from about 15° C. to about 95° C. in the presence of the de-waxing agent. In addition, the use of poly (organosiloxane)s is also compatible with a variety of different protocols known from the state of the art for further processing the de-waxed biological material, e.g. QIAamp DNA FFPE kit, EpiTect Plus FFPE Bisulfite kit.

Thus, the present invention relates to a method for processing a wax-embedded biological sample, comprising a step (1) of liquefying the embedding medium by exposing the embedded biological sample to a de-waxing agent, wherein the de-waxing agent comprises a poly(organosiloxane) or a mixture of poly(organosiloxane)s.

In terms of the present invention the term "exposing the embedded biological sample to a de-waxing agent" comprises any step of bringing the embedded biological sample into contact with the de-waxing agent, i.e. by adding the de-waxing agent to the embedded biological sample or vice versa. For example, the embedded biological sample may be immersed into the de-waxing solution. Alternatively, an amount of the de-waxing solution sufficient to completely coat the embedded sample may be added to said sample, for example by pipetting. It should be understood that the wax embedding the biological sample preferably is in the solid state until being contacted with the de-waxing agent. In order to accelerate the process of liquefying and/or solubilizing the embedding medium, mixing of the de-waxing agent and the embedded biological sample may be enhanced by stirring, vortexing, agitating, pipetting, using ultrasonics and the like. Alternatively or in addition, heat may be applied. In particular if not an histological analysis of a tissue section, but analysis of specific biomolecules present in a lysate obtained by lysis the de-waxed biological sample is of interest, the embedded biological sample may also be mechanically disrupted prior to or while being exposed to the de-waxing agent, for example by homogenization, vortexing, or the like. For thicker material, e.g. core needle punches, mechanical disruption by bead mill or polytron devices may be useful.

A particular advantage of the use of poly(organosiloxane)s for de-waxing is the fact, that after liquefying the embedding medium, an aqueous solution may be added to the sample still comprising the liquefied embedding medium. As the aqueous solution is not miscible with the poly(organosiloxane) phase, the latter comprising the liquefied embedding medium, two immiscible liquid phases are obtained. These phase may be easily separated using standard techniques known in the state of the art, such as for example decanting, pipetting, and the like, without being limited to these. If, for instance, an aqueous lysis buffer is added to the sample still comprising the liquefied embedding medium dissolved in said poly(organosiloxane)(s), even lysis of the biological sample may be accomplished in the resulting biphasic mixture without compromising the lysis result. As most parts of the biological sample (or its components, respectively, such as for example nucleic acids released during lysis) pass into the aqueous phase, the desired biological material may be easily separated from the liquefied embedding medium using standard techniques for liquid-liquid phase separation.

Using the method of the present invention, neither toxic and/or flammable organic solvents, such as for example xylene, nor laborious washing steps are necessary to liquefy and remove the embedding medium from a wax-embedded biological sample.

As poly(organosiloxane)s are rather chemically inert, even at elevated temperatures, e.g. 100° C. and above, the biological sample may even be subjected to heating steps in the presence of the liquefied embedding medium, for example for removing cross-linkings from formalin-fixed samples, which may be carried out by heating the sample to about 70 to about 95° C. In that scenario, the poly(organosiloxane) also serves to limit evaporation of the sample buffer.

In terms of the present invention the term "about" is used to indicate an error margin of the respective value up to 5%.

In the present invention, it is particularly preferred to use poly(organosiloxane)s having a rather low kinematic viscosity at room temperature (23 +/−2° C.), while still having a rather high boiling point in comparison to non-polar organic solvents of comparable viscosity. Such de-waxing agents having a low viscosity (e.g. <5 $mm^2·s^{-1}$) but a rather high boiling point (e.g. >90° C., preferably >120° C.) are well suited for automatization of sample processing, e.g. using pipetting robots. Mixtures of different poly(organosiloxane)s may be employed as well. In this case, the mixture preferably may have a kinematic viscosity of 5 $mm^2·s^{-1}$ or less, whereas single components present in the mixture may have a kinematic viscosity higher than 5 $mm^2·s^{-1}$. The kinematic viscosity is the measure of volume flow in a liquid, given in Stokes (St.), a Stoke equaling 1 $cm^2·s^{-1}$, one centistoke (1 cSt=0.01 St) equaling 1 $mm^2·s^{-1}$. The kinematic viscosity (in Stokes) can be converted to viscosity, being a measure of the mass flow of the liquid (in Poise; 1 Poise equaling 0.1 Pas in SI-units) by multiplying by the density of the fluid.

Octamethyltrisiloxane, for instance, has a kinematic viscosity of about 1 $mm^2·s^{-1}$ (1 cSt), equal to water, while having a boiling point of 153° C. Due to its low viscosity, its density of 0.82 g/mL at 25° C., and its rather high boiling point, it can easily be both, added to and removed from a sample, even by automatic systems comprising a dosing unit, for example a pipetting automat.

Accordingly, the method of the present invention may preferably represent an automated method. In terms of the present invention, an "automated method" is a method in which at least one of the steps comprised in said method is carried out automatically, i.e. essentially machine or computer driven without direct human action (apart from any necessary initial set up). The method of the present invention can easily be carried out on a number of known workstations for automated sample processing, including for example the QIAsymphony SP. The low viscosity of the de-waxing agent does not only facilitate its delivery and removal and thus automatization of the method, but also ensures its fast spreading over the sample as well as its penetration into a sample tissue.

In terms of the present invention, the term "poly(organosiloxane)" refers to a compound or a mixture of compounds containing directly alternating silicon and oxygen atoms in a linear, branched or cyclic arrangement with one or more organic groups attached to each silicon atom. The poly(organosiloxane)s of the present invention preferably are lipophilic compounds not miscible with water. Examples of poly(organosiloxane)s include polydimethylsiloxanes, polydiethylsiloxanes, methyl hydrogen polysiloxanes, methyl alkyl polysiloxanes, methyl aryl polysiloxanes, methyl fluoroalkyl polysiloxanes, fluoro silicone fluids like e.g. trifluoropropyl heptamethyl trisiloxane, and organofunctional methylpolysiloxanes such as aminoalkyl methyl polysiloxanes, cyanoalkyl methyl polysiloxanes, haloalkyl methyl polysiloxanes, and vinyl methyl polysiloxanes, without being limited to these. Preferred siloxanes are insoluble in water. Furthermore preferred siloxanes are liquid at room temperature (23 +/−2° C.).

In terms of the present invention "alkyl" means any linear, branched or where appropriate cyclic hydrocarbon having e.g. 1, 2, 3, 4, 5, 6, 7, 8, 9 or 10 C-atoms, and "aryl" means an unsaturated hydrocarbon ring(system) having 3, 4, 5, 6, 7, 8, 9, 10, 11, 12 or more, preferably 5, 6, 9, 10, 13 or 14 members, wherein at least one C might be replaced by a heteroatom like N or S.

Examples of cyclic polysiloxanes may include octamethylcyclotetrasiloxane (D 4), decamethylcyclopentasiloxane (D 5), and dodecamethylcyclohexasiloxane (D 6). However, linear poly(organosiloxane)s may be preferred. Preferred examples of linear unbranched poly(organosiloxane)s include trimethylsiloxy-terminated polydimethylsiloxanes, in particular hexamethyldisiloxane (L 2), octamethyltrisiloxane (L 3), decamethyltetrasiloxane (L 4), and dodecamethylpentasiloxane (L 5).

Particularly preferred are trisiloxane fluids of low viscosity, e.g. 3-octylheptamethyltrisiloxane (having a kinematic viscosity of 3 mm$^2$·s$^{-1}$), 3-phenylheptamethyltrisiloxane (having a kinematic viscosity of 2 mm$^2$·s$^{-1}$), trifluoropropylheptamethyltrisiloxane (having a kinematic viscosity of 2 mm$^2$·s$^{-1}$), chloromethylheptamethyltrisiloxane (having a viscosity of 1 mm$^2$·s$^{-1}$), or octamethyltrisiloxane (L 3) (having a kinematic viscosity of 1 mm$^2$·s$^{-1}$), octamethyltrisiloxane (L 3) being particularly preferred.

Further examples may include polydimethylsiloxane oil, methyl hydrogen polysiloxane oil, methyl phenyl silicone oil, fluorine-modified silicone oil, amino-modified silicone oil, epoxy-modified silicone oil, hydroxy-modified silicone oil, and silicone oil modified by organic groups, such as alkyl-modified silicone oils. These oils usually represent a mixture the above mentioned poly(organosiloxane)s of different chain length.

The de-waxing agent used in the method of the present invention may comprise or preferably consist of one of the aforementioned poly(organosiloxane)s or a mixture of two or more of these poly(organosiloxane)s. In said mixtures, each poly(organosiloxane) independently may be linear, cyclic, or branched. Single poly(organosiloxane)s as well as mixtures of two or more different poly(organosiloxane)s are commercially available, for example from Sigma-Aldrich, St. Louis, Mo., USA. Mixtures of one or more poly(organosiloxane)s and one or more other lipophilic non-silicon containing compound(s) may be employed as well, including for example organic solvents miscible with the poly(organosiloxane)s, lipophilic dyes. Preferably, the de-waxing agent used in the present invention does neither comprise any hydrophilic components nor components comprising a hydrophilic portions, such as for example surfactants. The de-waxing agent used in the present invention preferably represents, more preferably is consisting of, a lipophilic compound or mixture of lipophilic compounds not soluble in or miscible with water. In particular, the de-waxing agent used in the present invention preferably does not represent an emulsion. It should be noted that even though the de-waxing agent used in the method of the present invention should be liquid at room temperature, single components present in the mixture employed as de-waxing agent may nevertheless represent compounds which are solid in the pure form at room temperature, e.g. hexamethylcyclotrisiloxane (D 3), provided that the mixture as a whole is liquid at room temperature.

In terms of the present invention, the term "wax-embedded sample" comprises any biological sample embedded in a wax, for example for histochemical and/or microscopic analysis. The wax usually comprises or consists of a complex mixture of higher hydrocarbons, is solid at room temperature and may include further components, such as esters of higher fatty acids, glycols and the like. The wax may be of natural and/or synthetic origin and may additionally contain additives enhancing its sample-embedding properties, such as for example small amounts of DMSO, higher polyolefins or other organic polymers. Preferably, the wax may represent paraffin. Paraffin is a mixture of primarily saturated hydrocarbons which is solid at room temperature. Paraffin usually is prepared by distillation of petroleum. Independently of which type of paraffin is used, so-called high melting or low melting paraffin or a mixture thereof, the sample may be processed using the method and/or the kit of the present invention.

The biological sample may represent a whole organism, or a part of an organism, in particular a tissue fragment or a tissue section, originating from humans, animals or plants, or microorganisms such as for example bacteria, viruses or fungi. Embedded cells, isolated for example from cell cultures or swabs, blood or other body fluids may be used as well. The wax-embedded biological sample to be processed according to the present invention preferably is selected from the group comprising embedded tissues and/or cells. Preferably said sample represents a paraffin-embedded sample, more preferably a formalin-fixed paraffin-embedded sample (FFPE-sample).

The de-waxing agent used in the method of the present invention preferably has a boiling point above 75° C., more preferably above 90° C., even more preferably above 120° C. and most preferably above 140° C. Unless indicated otherwise, the values for all physical variables are determined at a pressure of 1013.25 millibars, and (where applicable) room temperature. The use of chemically inert poly(organosiloxane)-based de-waxing agent having a rather high boiling point minimizes the risk that the embedding medium may re-solidify upon unintended evaporation of the solvent/de-waxing agent and thus allows a convenient sample handling, and also minimizes exposure of the user to solvent vapors. In addition, the sample may even be heated in the dewaxing agent, e.g. for thermally removing cross-linkings present in the sample as a result of formalin fixation. In addition, it is preferred that the de-waxing agent has a pour point (determined according to DIN/ISO 3016) below 0° C., preferably below −20° C., more preferably below −40° C., even more preferably below −60° C. and most preferably below −80° C. The pour point of a liquid is the lowest temperature at which it will pour or flow under prescribed conditions.

The de-waxing agent preferably has a kinematic viscosity of equal to or less than 5 $mm^2 \cdot s^{-1}$, preferably of equal to or less than 3 $mm^2 \cdot s^{-1}$, more preferably of equal to or less than 2 $mm^2 \cdot s^{-1}$ and most preferably of equal to or less than 1.5 $mm^2 \cdot s^{-1}$. The lower the kinematic viscosity of the de-waxing agent, the easier said agent can be both, added to and removed from the sample, e.g. by pipetting. Particularly preferred are de-waxing agents having a kinematic viscosity comparable to that of water, i.e. of from about 0.8 to about 1.2 $mm^2 \cdot s^{-1}$, preferably of from about 0.9 to about 1.1 $mm^2 \cdot s^{-1}$ and most preferably equal to about 1 $mm^2 \cdot s^{-1}$.

The poly(organosiloxane)(s) comprised in or forming the de-waxing agent of the present invention preferably is (are) selected from the group comprising linear poly(organosiloxane)s, preferably trialkylsiloxy-terminated polydialkylsiloxanes wherein "alkyl" comprises preferably linear or branched $C_1$, $C_2$, $C_3$, $C_4$ $C_5$ or $C_6$ hydrocarbon chains, more preferably from the group comprising linear trimethylsiloxy-terminated polydimethylsiloxanes of the formula $CH3[Si(CH3)2O]nSi(CH3)3$, wherein n is the number of repeating units. Preferably n is in the range of from 1 to 5. Most preferably, the poly(organosiloxane) represents octamethyltrisiloxane (n=2). As already described above, the de-waxing agent may also consist of a mixture of different poly(organosiloxane)s. The de-waxing agent further may comprise one or more poly(organosiloxane)s in combination with non-silicon-containing compounds, such as for example lipophilic organic solvents. It may, however, particularly be preferred that the de-waxing agent essentially consists of one single poly(organosiloxane), i.e. the de-waxing agent comprises at least 95% (wt/wt), preferably at least 97% (wt/wt) of said poly(organosiloxane). Most preferably, the de-waxing agent may consist essentially of octamethyltrisiloxane.

The amount of de-waxing agent added to a wax-embedded sample depends from the kind and amount of the wax-embedded sample, which is well known to a person skilled in the art. The amount of de-waxing agent should be high enough to at least completely cover the sample to be de-waxed. Of course, the necessary amount also depends on the vessel or tube in which the sample is processed, but can be easily determined. For example, a typical microtome section of FFPE tissue having a thickness of 5-20 µm, 1-2 cm across may be de-waxed using 250 to 750 µL of de-waxing agent, preferably 300 to 500 µL, when processed in standard 1.5-2 ml laboratory sampling tubes or multi-well plates.

In the method for processing a wax-embedded biological sample according to the present invention it may be preferred, that the step of exposing the embedded biological sample to a de-waxing agent includes incubating the embedded biological sample in the presence of the de-waxing agent at a temperature in the range of from about 15 to about 95° C., preferably of from about 20 to about 75° C. and most preferably of from about room temperature (23 +/−2° C.) to about 65° C. During incubating, mechanically mixing by shaking, vortexing, pipetting, and the like may be employed. Incubating preferably may be carried out for about 5 seconds to 12 hours, more preferably for about 10 seconds to about 3 hours, even more preferably for about 30 seconds to about 1 hour, still more preferably for about 45 seconds to about 30 min, and most preferably for about 1 to about 15 minutes.

The method of the present invention preferably further includes a step (2) of exposing the sample obtained in step (1), which still comprises the liquefied embedding medium, to an aqueous solution, thereby partitioning or separating the liquefied embedding medium and the de-waxed sample. The biological sample (or its components, respectively) essentially pass(es) into the aqueous phase, while the liquefied embedding medium essentially remains in the phase comprising the de-waxing agent. The biological sample and the liquefied embedding medium are present in two different liquid phases and thus are essentially separated from each other, even though the aqueous phase and the de-waxing agent may still be in physical contact with each other. Thus, the de-waxing agent separates from the sample upon contact with the aqueous solution and lifts up to the surface of the aqueous solution, if a de-waxing agent having a density lower than water is employed, i.e. below 1.00 g/mL at room temperature. To enhance dissolution of the paraffin and separation, physical mixing may be employed, e.g. by shaking, vortexing, pipetting, and the like, without being limited to these.

Surprisingly, no alcohol washing steps are necessary for removing the liquefied wax and/or dewaxing agent from the sample, which usually are employed in many methods known from the state of the art. This clearly accelerates and simplifies any method for processing a wax-embedded biological sample which comprises a step of removing the embedding medium. In addition, the amount of waste is reduced.

The aqueous solution to which the sample is exposed preferably may represent an aqueous lysis buffer, which preferably may comprise at least one buffering substance and a detergent. The buffering substance preferably keeps the pH of the aqueous solution in the range of between 4 and 9. A mixture of different buffering substances may be employed as well. The detergent may be non-ionic, cationic, anionic, or zwitterionic. A mixture of different detergents may be employed as well. Preferred buffering agents and surfactants are e.g. TRIS, MOPS, MES, HEPES and Tween-20, SDS, Triton X-100 or similar, respectively etc. Further the lysis buffer may comprise at least one nucleophilic reagent.

Suitable as nucleophilic reagent in this connection are all Lewis bases able to transfer electrons into an empty orbital or into empty orbitals of a Lewis acid. Particularly preferred Lewis bases among these are reagents which have at least one functional group which carries a negative charge, which is negatively polarized or which has at least one free electron pair.

Compound comprising a functional group having a negative charge are for example alkali metal or alkaline earth metal oxides, alkali metal or alkaline earth metal hydroxides, alkali metal or alkaline earth metal halides, alkali metal or alkaline earth metal cyanides and the like.

Reagents having at least one functional group which is negatively polarized are in particular reagents having at least one functional group in which two atoms which differ in their Alfred and Rochow electron negativity by at least 0.25, particularly preferably by at least 0.5 and further preferably by at least 1.0 are covalently connected together.

However, nucleophilic reagents which are particularly preferred according to the invention are those having at least one functional group with one or two, particularly preferably with one free electron pair, and the most preferred among these compounds in turn are those having at least one primary, secondary or tertiary amino group of the structure I $$R1-NR2R3 \tag{I}$$

in which R1 is a $C_1$ to $C_{20}$ hydrocarbon group, particularly preferably a $C_2$ to $C_{15}$ hydrocarbon group and further preferably a $C_2$ to $C_{10}$ hydrocarbon group, a $C_1$ to $C_{20}$ hydrocarbon group having at least one heteroatom, a $C_2$ to $C_{15}$ hydrocarbon group having at least one heteroatom and further preferably a $C_2$ to $C_{10}$ hydrocarbon group having at least one heteroatom, or an optionally heteroatom-substituted aromatic ring system, R2 is a $C_1$- to $C_{20}$-alkyl group, particularly preferably a $C_1$- to $C_{10}$-alkyl group and further preferably a $C_1$- to $C_2$-alkyl group, in particular a methyl group or an ethyl group, a $C_1$- to $C_{20}$-hydroxyalkyl group, particularly preferably a $C_1$- to $C_{10}$-hydroxyalkyl group and further preferably a $C_1$- to $C_2$-hydroxyalkyl group, or a hydrogen atom, with a hydrogen atom being most preferred, and R3 is a $C_1$- to $C_{20}$-alkyl group, particularly preferably a $C_1$- to $C_{10}$-alkyl group and further preferably a $C_1$- to $C_2$-alkyl group, in particular a methyl group or an ethyl group, a $C_1$- to $C_{20}$-hydroxyalkyl group, particularly preferably a $C_1$- to $C_{10}$-hydroxyalkyl group and further preferably a $C_1$- to $C_2$-hydroxyalkyl group, or a hydrogen atom, with a hydrogen atom being most preferred.

Nucleophilic reagents which are particularly preferred according to the invention and have a functional group of structure I depicted above are in particular those which have at least one functional group of structure I in which at least one of the radicals R2 and R3, most preferably both radicals R2 and R3 is or are a hydrogen atom. Further particularly preferred nucleophilic reagents are those having at least one functional group of structure I in which the nitrogen atom is covalently linked only to those atoms in the radicals R1, R2 and R3 which are sp³ hybridized. In particular, none of the radicals R1, R2 or R3 should be able to delocalize the free electron pair on the nitrogen atom beyond the radicals R1, R2 and R3. Thus, it is particularly preferred for none of the radicals R1, R2 and R3 to have for example structure II

—C(=NH)NH₂                   (II)

Nucleophilic reagents which are particularly preferred according to the invention and have at least one functional group of structure I are selected from the group consisting of methylamine, ethylamine, ethanolamine, n-propylamine, n-butylamine, isobutyl-amine, tert-butylamine, dimethylamine, diethylamine, diethanolamine, di-n-propylamine, diisopropylamine, dibutylamine, trimethylamine, triethylamine, triethanolamine, hexamethylenetetramine, 2-ethylhexylamine, 2-amino-1,3-propanediol, hexylamine, cyclohexylamine, 1,2-dimethoxypropanamine, 1-amino-pentane, 2-methyloxypropylamine, tri(hydroxymethyl)aminomethane, amino carboxylic acids, in particular glycine or histidine, or aminoguanidine, and among these ethanolamine, diethanolamine, triethanolamine, amino-1,3-propanediol, aminoguanidine and tri(hydroxymethyl)aminomethane are most preferred. Further preferred nucleophilic reagents having at least one functional group of structure I are aromatic amines selected from the group consisting of aniline, toluidine, naphthylamine, benzylamine, xylidene, xylene-diamines, naphthalenediamines, toluenediamines, 3,3'-dimethyl-4,4'-diphenyldiamine, phenylenediamines, 2,4'-methylenedianiline, 4,4'-methylenedianiline, sulfonyldianiline, and dimethylbenzylamine.

The nucleophilic reagent may have at least one primary amino group of structure I, the nucleophilic reagent is a C 1- to C 6-alkylamine, a C 1- to C 6-alkyldiamine, a C 1- to C 6-alkyltriamine, a C 1 to C 15 amino alcohol or a C 1 to C 15 amino diol, or a C 1 to C 15 amino carboxylic acid.

The nucleophilic reagent further may be a heterocyclic compound comprising a nitrogen atom selected from the group comprising pyrrole, pyridine, quinoline, indole, azacyclopentane, azacyclohexane, morpholine, piperidine, imidazole or a derivative of these compounds, where a derivative of these compounds preferably means a derivative in which a C 1- to C 3-alkyl group, particularly preferably a methyl group or ethyl group, is bonded instead of a hydrogen atom to one or more carbon atoms or to the nitrogen atom in the aforementioned compounds.

Particularly preferred nucleophilic reagents among those abovementioned are in particular those which are soluble in water, especially those which show a solubility of at least 1 g/L, particularly preferably at least 10 g/L and further preferably at least 100 g/L, in water at a temperature of 25 degrees C. and at a pH of 7.

The preferably aqueous solution comprising the nucleophilic reagent described above may be based on pure, preferably deionized water or else on other aqueous systems, in particular on mixtures of water and organic solvents such as alcohols, especially mixtures of water and ethanol or methanol, with the amount of water preferably being at least 50 percent by weight, particularly preferably at least 75 percent by weight and most preferably at least 90 percent by weight, in each case based on the total weight of water and organic solvent, physiological saline solutions, on buffers, especially buffers comprising buffer components known to the skilled worker, such as, for example, TRIS, HEPES, PIPES, CAPS, CHES, AMP, AMPD or MOPS in an amount in a range from 0.1 to 1000 mmol/l, particularly preferably 1 to 500 mmol/l and most preferably 10 to 200 mmol/l, it being possible where appropriate for such a buffer component, depending on the structure thereof, also to serve simultaneously as nucleophilic reagent. A further possibility is also to employ nutrient media such as, for instance, MEM medium and DMEM medium, as aqueous system. The aqueous solution comprising the nucleophilic reagent is preferably prepared simply by mixing water or an appropriate aqueous system with the nucleophilic reagent.

The concentration of the nucleophilic reagent in the aqueous solution is preferably in a range from 0.1 to 10 000 mmol/l, further preferably from 1 to 5000 mmol/l, further even more preferably from 5 to 2500 mmol/l and most preferably from 20 to 1000 mmol/l. In a particularly advantageous embodiment of the method of the invention, the concentration of the nucleophilic reagent in the aqueous solution is more than 20 mmol/l, particularly preferably more than 50 mmol/l and most preferably more than 100 mmol/l.

The pH of the aqueous solution is preferably in a range from 2 to 12, particularly preferably from 4 to 9 and most preferably from 5 to 8, in each case measured at room temperature.

Further according to the method of the invention the biological sample can be contacted, preferably incubated, with compounds which promotes the destruction of a biological tissue and/or the lysis of cells. This compound preferably being an enzyme, a detergent, a chaotropic substance or a mixture of at least two of these components.

Enzymes preferred in this connection are in particular proteases, and among these trypsin, proteinase K, chymotrypsin, papain, pepsin, pronase and endoproteinase lys-C are particularly preferred, and proteinase K is most preferred. In a particular embodiment of the method of the invention, however, it is also possible to employ as enzyme a thermostable protease as described for instance in WO-A-91/19792 (isolated from *Thermoccus celer, Thermococcus* sp.AN1, *Thermococcus stetteri* or *Thermococcus litoralis*) or in WO-A-91/19792 (isolated from *Staphylothermus marinus*). The disclosure of these publications relating to thermostable proteases is hereby introduced as reference and forms part of the disclosure of the present invention.

In an embodiment of the method of the invention which can be used for analyzing proteins from the fixed sample, no compound having proteolytic activity, such as a protease, is employed. In an embodiment wherein nucleic acids shall be analyzed no nuclease such as a DNase and/or RNas, shall be contained.

The concentration of the enzyme in the aqueous solution is preferably in a range from 0.001 to 5 percent by weight, particularly preferably 0.01 to 2.5 percent by weight and most preferably 0.05 to 0.2 percent by weight, in each case based on the total weight of the aqueous solution.

Detergents preferably employed are compounds selected from the group comprising sodiumdodecylsulfate (SDS), polyethylene glycol phenol ethers such as, for example, Triton-X-100, Tween, NP-40 or mixtures thereof, with SDS and Triton-X-100 being particularly preferred as detergents. The amount of detergent employed to lyse the cells present in the biological sample depends on the nature and amount of the biological sample and can be ascertained by the skilled worker by simple routine experiments.

Lysis of the de-waxed biological sample preferably may be carried out in presence of the de-waxing agent comprising the liquefied embedding medium. Preferably lysis may be carried out by incubating the mixture obtained in step (2), which comprises the aqueous lysis buffer, comprising the de-waxed biological sample, and the de-waxing agent, encompassing the liquefied embedding medium. Incubation preferably may be carried out at a temperature or a succession of temperature steps in the range of from about 15 to about 95° C., more preferably of from about 20 to about 90° C. Incubation preferably may be carried out for a time period of from about 1 minute to about 24 hours, more preferably of from about 5 minutes to about 12 hours, and most preferably of from about 15 minutes to about 3 hours. By "succession of temperature steps" it is meant that the temperature at which the mixture is incubated may be varied during incubation, i.e. the mixture may be incubated at two or more different temperatures consecutively, both or all of which are in the range of from about 15 to about 95° C., preferably of from about 20 to about 90° C. For instance, the mixture may be incubated first at a temperature of about 50 to about 65° C. for e.g. about 10 to about 30 min or up to 24 h, and the temperature may then be raised to for example about 70 to about 95° C., the sample being kept at that temperature for about 10 to about 30 min. Such a succession of temperature steps may be particularly preferred, if a protease is added to the sample.

In addition, it should be understood, that any step of the present invention as well as two or more of these steps may be carried out at an elevated temperature, i.e. a temperature above room temperature. Said temperature preferably may be in the range of from above room temperature and equal to or below about 95° C., e.g. at 25° C., 30° C., 35° C., 37° C., 40° C., 45° C., 50° C., 55° C., 60° C., 65° C., 70° C., 75° C., 80° C., 85° C., or 90° C. In order to carry out a step at an elevated temperature, the sample itself may be heated to said temperature and/or any agent combined with the sample during processing may be heated prior to combining it with the sample.

If histological staining of the de-waxed sample is envisaged, the aqueous solution preferably may represent an aqueous staining solution, which comprises a dye or a substance, which preferentially binds to a certain type of cell and/or cell component. Such histologicals stains may comprise acridine dyes, anthraquinone dyes, arylmethane dyes, azo dyes, diazonium dyes, nitro dyes, phthalocyanine dyes, quinine imine dyes, tetrazolium dyes, thiazole dyes and/or xanthene dyes. Histological stains may also include hematoxylin and eosin or cresyl violet Without being limited to these. Preferably a proteolytic agent may be present during the aforementioned lysis step. Accordingly, the aqueous lysis buffer described above either additionally may comprise a proteolytic agent or a proteolytic agent may be added to the mixture of the aqueous lysis buffer and the de-waxing agent obtained in step (2). Said proteolytic agent preferably may be selected from the group comprising proteases and non-enzymatic proteolytic compounds. More preferably said proteolytic agent may represent proteinase K, trypsin, chymotrypsin, papain, pepsin, pronase, endoproteinase Lys-C, alpha-lytic proteinase, elastase, collagenase, bromocyane, recombinant *Bacillus proteases*, Lysozyme, or a mixture thereof.

Preferably, the method for processing a wax-embedded biological sample according to the present invention additionally may comprise an optional step (3) of reducing the number of remaining cross-linkings in the sample, preferably by heating the mixture of the aqueous lysis buffer and the de-waxing agent to a temperature of about 70 to about 95° C. and/or by adding to said mixture a cross-linking removal agent, comprising at least one nucleophilic reagent as mentioned above.

Preferably, the method for processing a wax-embedded biological sample according to the present invention may comprise an additional step of (4) optionally separating the aqueous phase from the de-waxing agent, the latter comprising the liquefied embedding medium. Preferably, the method for processing a wax-embedded biological sample according to the present invention also may comprise an additional step of (5) selectively isolating at least one class of biomolecules, selected from the group comprising proteins, RNA and DNA, preferably representing single and/or double-stranded RNA (ssRNA and dsRNA, respectively), including messenger RNA (mRNA), transfer RNA (tRNA), ribosomal RNA (rRNA), micro RNA (miRNA), and/or small nuclear RNA (snRNA), other (short or long) non-coding RNA, and/or single and/or double-stranded DNA (ssDNA and dsDNA, respectively), including genomic DNA (gDNA), complementary DNA (cDNA), mitochondrial DNA (mDNA), small nuclear DNA (snDNA), and plasmid DNA, from the lysed biological sample.

It should be understood that the numbers (1) to (5) are used only to indicate the order in which these steps (if present) are carried out. It does, however, not imply that all of steps 1 to 5 have to be present in every embodiment of the method of the present invention. The methods of the present invention also may include embodiments which may comprise steps (1) and (2), but not steps (3), (4), and (5); steps (1), (2) and (3), but not steps (4) and (5); steps (1), (2), (3), and (4), but not step (5); steps (1), (2), (3), and (5), but not step (4); (1), (2) and (4), but not steps (3) and (5); (1), (2), (4), and (5), but not step (3); (1), (2) and (5), but not steps (3) and (4). Furthermore, one or more intermediate step(s) may be present between two of the consecutively numbered steps listed above. If, for instance, the isolation of RNA from the sample is envisaged, a step of digesting DNA present in the sample, e.g. using a DNase, may be employed after separating the aqueous phase from the de-waxing agent according to step (4), but before selectively isolating and purifying the RNA from further components present in the sample, i.e. by selectively binding it to a silica membrane in the presence of chaotropic salts. Alternatively, an so-called "on-column DNA digest" may be carried out while the RNA is already bound to the silica membrane. However, de-waxing steps employing xylene or alcoholic washing steps before contacting the sample with the aqueous staining solution or aqueous lysis buffer preferably not included in the method of the present invention. This does, however, not exclude alcoholic washing steps after separating the aqueous solution from the de-waxing agents, such as for example ethanol washing steps for selectively precipitating nucleic acids to a silica membrane during purification.

In order to facilitate optical detection and monitoring of phase separation, the de-waxing agent may comprise a lipophilic dye, which is soluble in the de-waxing agent, but insoluble in the aqueous buffer. Preferably, the step of (5) isolating at least one class of biomolecules may comprise at least one chromatographic and/or solid phase-based purification step, binding to magnetic beads, or solid phase-based precipitation step. Preferably said chromatographic and/or solid phase-based purification or precipitation step may be selected from the group comprising (a) gel filtration chromatography, (b) ion exchange chromatography, (c) reversed phase chromatography, and (d) precipitating and binding to a solid phase, preferably a silica phase. Such methods are known in the state of the art. In terms of the present invention the term "precipitating and binding to a solid phase" refers to any solid-phase based method in which biomolecules, in particular nucleic acids are precipitated from solution in the presence of a solid phase by adding a precipitating agent, so that the biomolecules of interest selectively precipitate on the solid phase and thus are bound to said solid phase. The solid phase may be present in the form of a membrane, a column filling, a filter, beads, particles, a surface coating, a dip-stick, or a rod, without being limited to these. If employing particles or beads, preferably magnetic particles or beads may be used as a solid phase in order to facilitate separation from the liquid phase(s). The solid phase may represent silica, silicon, glass, plastic, nitrocellulose, polyvinylidene fluoride (PVDF), or nylon, silicon carbide, aluminum and other metal oxide without being limited to these. The surface of said solid phase may optionally be functionalized by functional groups in order to tune or enhance the selectivity and/or strength of binding to the biomolecules, which is well known to a person in the art.

Particularly preferred may be solid phases made of silica, to which nucleic acids may be bound selectively in the presence of chaotropic binding buffers. A series of kits for purifying nucleic acids from an aqueous solution, in particular a cell lysate based on this principle are commercially available and may be employed in the method of the present invention, including for example the QIAGEN RNeasy QIAamp FFPE DNA, EpiTect FFPE, QIAsymphony RNA kits from QIAGEN, Hilden, Germany. The present invention further relates to the use of a poly(organosiloxane) or a mixture of poly(organosiloxane)s for liquefying the embedding medium in a wax-embedded biological sample.

The present invention further relates to a kit for processing a wax-embedded biological sample, comprising (1) a de-waxing agent which comprises a poly(organosiloxane) or a mixture of poly(organosiloxane)s, and (2) at least one further component selected from the group comprising (a) an aqueous solution for partitioning the de-waxed sample and the liquefied embedding medium, (b) a chromatographic device and/or a solid phase for isolating at least one class of biomolecules, and (c) instructions for using the kit.

The kit of the present invention preferably may be a kit for processing a wax-embedded biological sample according to the method of the present invention as described above. In said kit the poly(organosiloxane)(s) preferably may represent poly(organosiloxane)s as described above. In said kit the aqueous solution preferably may represent a lysis buffer as described above. In said kit the chromatographic device and/ or solid phase preferably may represent a chromatographic device and/or solid phase for carrying out a chromatographic and/or solid phase-based purification or precipitation step as described above, preferably selected from the group (a) comprising gel filtration chromatography, (b) ion exchange chromatography, (c) reversed phase chromatography and (d) precipitating and binding to a solid phase.

EXAMPLES

General Remarks

In all experiments, tissue sections having a thickness of 5 μm, obtained from formalin-fixed, paraffin-embedded human tissue blocks (kidney and liver, respectively) were employed, which had been stored at room temperature for at least 26 month. Unless indicated otherwise, each experiment was carried out in triplicate. Lysis and digestion solutions, binding, wash and elution buffers and the spin columns used are commercially available from QIAgen (Hilden, Germany).

As de-waxing agents, hexadecane (A; comparative example), mineral oil (B; comparative example) and silicone oil (C; according to the present invention, octamethyltrisiloxane 98% (Sigma-Aldrich, St. Louis, Mo., USA)) were used.
General Protocol for De-Waxing and Cell Lysis:

1. 400 μL of one of the de-waxing agent as indicated above (A, B, or C, respectively) were added to one section of FFPE tissue. The mixture was vortexed for 10 s, then shaken for another 10 s and finally centrifuged at full speed for 2 min at 20 to 25° C.
2. The mixture was incubated at 60° C. for 3 min and then vortexed for 10 s.
3. The mixture was left to stand in order to cool down to room temperature.
4. 150 μL of lysis buffer PKD (QIAgen) were added to the sample. The resulting mixture was vortexed for 10 s and then centrifuged at 11,000×g for 1 min at 20 to 25° C.
5. 10 μL Proteinase K (Qiagen, Hilden, Germany) were pipetted to the lower aqueous phase, and said phase was mixed by pipetting the phase up and down three times.
6. The sample was incubated for 15 min at 56° C., followed by a second incubation step at 80° C. for another 15 min.
7. The (lower) aqueous phase was separated using a pipette and transferred to a new tube.
8. The aqueous phase was incubated on ice for 3 min, and then centrifuged at 20,200×g for 15 min. The supernatant was transferred to a new tube, while the remaining pellet was discarded. Further processing of the samples was carried out according to the following examples 1 and 2, respectively.

Example 1

Isolation and Purification of Total RNA, Including miRNA, from FFPE Samples with on-Column DNA Digesting In this experiment liver samples were used. The samples were prepared as described in the above general protocol. Then 9. 320 μL of buffer RBC (QIAgen) were added to the sample obtained in the above step 8, and the mixture was vortexed thoroughly.
10. 1.12 mL of pure EtOH were added, and mixed with the sample by pipetting up and down.
11. 700 μL of the solution obtained in step 10 were applied to an RNeasy MinElute spin column equipped with a 2 mL collection tube (QIAgen). The column was centrifuged at 8,000×g for 15 s, and the flow-through was discarded.

12. Step 11 was repeated until the whole sample was transferred.
13. 350 μL of buffer RDF (QIAgen) were applied to the column, and the column was centrifuged at 8,000×g for 15 s. The flow-through was discarded.
14. For an on-column DNA digest, 80 μL of DNase I mix, comprising 10 μL of DNase 1 (2.7 Kunitz units/μl) and 70 μL of buffer RDD (QIAgen), were applied directly to the silica membrane. The membrane was incubated for 15 min at room temperature.
15. 500 μL buffer RDF (QIAgen) were added to the column, and the column was centrifuged at 8,000×g for 15 s. The flow-through was collected.
16. The spin column was placed into a new 2 mL collection tube, and the flow-through collected in step 15 was applied to the column. The column was centrifuged at 8,000×g for 15 s, and the flow-through was discarded.
17. 500 μL buffer RPE (QIAgen) were added to the column, and the column was centrifuged at 8,000×g for 15 s. The flow-through was discarded.
18. 500 μL buffer RPE (QIAgen) were added to the column, and the column was centrifuged at 8,000×g for 2 min. The flow-through was discarded.
19. The spin column was placed into a new 2 mL collection tube. To dry the column, the open column was centrifuged at full speed for 5 min. The flow-through was discarded.
20. The column was placed in a 1.5 mL safe-lock tube (Eppendorf). RNA was eluted from the column by applying 20 μL RNase-free water to the membrane and centrifuging the column at full speed for 1 min. The flow-through was collected and analyzed as described below.

The eluates were analyzed UV/Vis-spectroscopically at a Nanodrop (ThermoSCIENTIFIC, Wilmington, Del., USA) following the manufacture's protocol. The mean RNA yield obtained from three individual liver samples were as follows: using hexadecane 0.56 μg, using mineral oil 0.49 μg, and using silicone oil 0.63 μg.

Individual samples were analyzed on an Agilent 2100 Bioanalyzer (Agilent, Waldbronn, Germany) according to the Agilent 6000 Nano Kit Guide, edition 08/2006. The RNA integrity number (RIN) were virtually the same for all the samples using mineral oil 1.20 and using silicone oil 1.20.

Real-time reverse-transcriptase-PCR was carried out on a Rotor-Gene Q (QIAgen, Hilden, Germany), using a QuantiTect Reverse Transcription Kit (QIAgen, Hilden, Germany) for DNA synthesis with integrated genomic DNA removal using gDNA Wipeout Buffer. 6.25 μL QuantiFast gDNA wipeout buffer (QIAgen) and 4.75 μL RNase-free water were mixed with 2 μL of the sample solution, which had been diluted using RNase-free water to obtain a RNA concentration of about 25 ng/μL or 2 μL RNA-free water as a blank, respectively. The mixtures were incubated at room temperature for 5 min.

Further sample processing was carried out on ice. 1.25 μL of the sample mixtures were mixed with 6.25 μL QuantiFast Probe RT-PCR Plus master mix (QIAgen), 1.25 μL of a forward primer and 1.25 μL of a reverse primer 0.25 μL QuantiTect Fast RT Mix (QIAgen) and 1.75 μL RNAse-free water (sample with reverse transcriptase), or 2.0 μL of RNAse-free water (samples without reverse transcriptase) were then added to the samples. The resulting PCR mixtures (12 μL) were transferred into PCR tubes and amplified. The thermal cycler conditions were as follows: 20 min at 50° C., melting for 5 min at 95° C., and then 40 cycles of 15 s at 95° C. and annealing and extending for 30 s at 60° C. The results obtained are presented in table 1.

TABLE 1

| De-waxing agent | w/o RT (mean value) | RT (mean value) | Δ ct |
|---|---|---|---|
| hexadecane | 40.00 | 33.49 | 6.51 |
| mineral oil | 40.00 | 32.28 | 7.72 |
| silicone oil | 40.00 | 33.45 | 6.55 |

Example 2

Isolation and Purification of Total RNA, Including miRNA, from FFPE Samples with Digesting DNA Before Applying the Samples to the Column In this experiment kidney samples were used. The samples were prepared as described in the above general protocol. Then 9. 16 μL of DNase booster buffer (QIAgen) and 10 μL of DNase (Qiagen) were added to the sample obtained in the above step 8. The mixture was incubated at 37° C. for 15 min.
10. 320 μL buffer RBC (QIAgen) were added and the mixture was vortexed thoroughly.
11. 1.12 mL of pure EtOH were added and mixed with the sample by pipetting up and down.
12. 700 μL of the solution obtained in step 11 were applied to an RNeasy MinElute spin column equipped with a 2 mL collection tube (QIAgen). The tube column was centrifuged at 8,000×g for 15 s, and the flow-through was discarded.
13. Step 12 was repeated until the whole sample was transferred.
14. 700 μL of buffer RDF (QIAgen) were applied to the column, and the column was centrifuged at 8,000×g for 15 s. The flow-through was discarded.
15. 500 μL of buffer RPE (QIAgen) were added to the column, and the column was centrifuged at 8,000×g for 15 s. The flow-through was discarded.
16. 500 μL of buffer RPE (QIAgen) were added to the column, and the column was centrifuged at 8,000×g for 2 min. The flow-through was discarded.
17. The spin column was placed into a new 2 mL collection tube. To dry the column, the open column was centrifuged at full speed for 5 min. The flow-through was discarded.
18. The column was placed in a 1.5 mL safe-lock tube. RNA was eluted from the column by applying 20 μL of RNase-free water to the membrane and centrifuging the column at full speed for 1 min. The flow-through was collected and analyzed as described below.

The eluates were analyzed UV/Vis-spectroscopically at a Nanodrop (ThermoSCIENTIFIC, Wilmington, Del., USA) following the manufacture's protocol. The mean RNA yield obtained from three individual kidney samples were as follows: using hexadecane 1.38 μg, using mineral oil 1.11 μg, and using silicone oil 1.89 μg.

Individual samples were analyzed on an Agilent 2100 Bioanalyzer (Agilent, Waldbronn, Germany) according to the Agilent 6000 Nano Kit Guide, edition 08/2006. The RNA integrity number (RIN) were as follows: using hexadecane 2.00, using mineral oil 2.50 and using silicone oil 2.50.

Real-time reverse-transcriptase-PCR was carried out on a Rotor-Gene Q (QIAgen, Hilden, Germany), using a QuantiTect Reverse Transcription Kit (QIAgen, Hilden, Germany) for DNA synthesis with integrated genomic DNA removal using gDNA Wipeout Buffer. Sample preparation for PCR and PCR were carried out as described in example 1. The results are presented in table 2.

TABLE 2

| De-waxing agent | w/o RT (mean value) | RT (mean value) | Δ ct |
|---|---|---|---|
| hexadecane | 40.00 | 33.08 | 6.92 |
| mineral oil | 40.00 | 32.29 | 7.71 |
| silicone oil | 40.00 | 32.85 | 7.15 |

As can been seen from the results of examples 1 and 2, silicone oil can be used for de-waxing of FFPE tissue samples with subsequent cell lysis in the presence of the de-waxing agent. The sample solutions obtained can processed further conveniently using well established commercially available purification and analysis kits. Nucleic acids, e.g. RNA, including miRNA, can be isolated from these samples in a yield and quality comparable and sometimes even superior to the results obtained using methods known in the state of the art.

The invention claimed is:

1. A method for processing a wax-embedded biological sample that comprises a biological sample and wax as an embedding medium, comprising:
   (1) liquefying the embedding medium by exposing the embedded biological sample to a de-waxing agent to obtain a de-waxed sample and a liquefied embedded medium, wherein the de-waxing agent comprises a poly(organosiloxane) or a mixture of poly(organosiloxane)s.

2. The method of claim 1, wherein the wax-embedded biological sample is selected from the group consisting of embedded tissues and cells.

3. The method of claim 2, wherein the wax-embedded biological sample is a paraffin-embedded sample.

4. The method of claim 2, wherein the wax-embedded biological sample is a formalin-fixed paraffin-embedded sample (FFPE-sample).

5. The method of claim 1, wherein the de-waxing agent has a boiling point above 75° C.

6. The method of claim 5, wherein the de-waxing agent has a boiling point above 90° C.

7. The method of claim 6, wherein the de-waxing agent has a boiling point above 120° C.

8. The method of claim 7, wherein the de-waxing agent has a boiling point above 140° C.

9. The method of claim 1, wherein the de-waxing agent has a kinematic viscosity of equal to or less than 5 $mm^2 \cdot s^{-1}$.

10. The method of claim 9, wherein the de-waxing agent has a kinematic viscosity of equal to or less than 3 $mm^2 \cdot s^{-1}$.

11. The method of claim 10, wherein the de-waxing agent has a kinematic viscosity of equal to or less than 2 $mm^2 \cdot s^{-1}$.

12. The method of claim 11, wherein the de-waxing agent has a kinematic viscosity of equal to or less than 1.5 $mm^2 \cdot s^{-1}$.

13. The method of claim 1, wherein the poly(organosiloxane)(s) is (are) selected from the group consisting of linear poly(organosiloxane)s.

14. The method of claim 13, wherein the poly(organosiloxane)(s) is (are) trialkylsiloxy-terminated polydialkylsiloxanes wherein "alkyl" comprises linear or branched $C_1$, $C_2$, $C_3$, $C_4$ $C_5$ or $C_6$ hydrocarbon chains.

15. The method of claim 14, wherein the poly(organosiloxane)(s) is (are) selected from the group consisting of linear trimethylsiloxy-terminated poly(dimethylsiloxane)s of the formula $CH_3[Si(CH_3)_2O]_nSi(CH_3)_3$, wherein the number of repeating units n is in the range of from 1 to 5.

16. The method of claim 15, wherein the poly(organosiloxane) is octamethyltrisiloxane (n=2).

17. The method of claim 1, wherein the step of exposing the embedded biological sample to a de-waxing agent comprises incubating the embedded biological sample in the presence of the de-waxing agent at a temperature in the range of from 15 to 95° C.

18. The method of claim 17, wherein the step of exposing the embedded biological sample to a de-waxing agent comprises incubating the embedded biological sample in the presence of the de-waxing agent at a temperature in the range of from 20 to 75° C.

19. The method of claim 18, wherein the step of exposing the embedded biological sample to a de-waxing agent comprises incubating the embedded biological sample in the presence of the de-waxing agent at a temperature in the range of from room temperature (23+/−2° C.) to 65° C.

20. The method of claim 1, further comprising:
   (2) exposing the mixture obtained in step (1) to an aqueous solution, thereby partitioning the liquefied embedding medium and the de-waxed biological sample.

21. The method of claim 20, wherein the aqueous solution is an aqueous lysis buffer, and lysis of the de-waxed biological sample is carried out in the presence of the de-waxing agent and the liquefied embedding medium to obtain a lysed biological sample.

22. The method of claim 21, wherein the aqueous lysis buffer comprises at least one buffering substance and a detergent.

23. The method of claim 21, wherein the lysis of the de-waxed biological sample is carried out by incubating the mixture obtained in step (2) at a temperature or a succession of temperature steps in the range of from 15 to 95° C. or from 20 to 90° C.

24. The method of claim 23, wherein the lysis of the de-waxed biological sample is carried out by incubating the mixture obtained in step (2) for a time period of from 1 minute to 24 hours, from 5 minutes to 12 hours, or from 15 minutes to 3 hours.

25. The method of claim 21, wherein either the aqueous lysis buffer additionally comprises a proteolytic agent or a proteolytic agent is added to the mixture obtained in step (2), said proteolytic agent being selected from the group consisting of proteases and non-enzymatic proteolytic compounds.

26. The method of claim 21, wherein the proteolytic agent is selected from the group consisting of proteinase K, trypsin, chymotrypsin, papain, pepsin, pronase, endoproteinase Lys-C, alpha-lytic proteinase, elastase, collegenase, bromocyane, recombinant Bacillus proteases, Lysozyme, and mixtures thereof.

27. The method of claim 21, further comprising:
   (3) reducing the number of remaining cross-linkings in the sample.

28. The method of claim 27, wherein step (3) is carried out by heating the mixture of the aqueous lysis buffer and the de-waxing agent to a temperature of about 70-95° C. and/or by adding to said mixture a cross-linking removal agent, comprising at least one nucleophilic reagent.

29. The method of claim 21, further comprising:
   (4) optionally separating the aqueous phase from the de-waxing agent and the liquefied embedding medium, and (5) selectively isolating at least one class of biomolecules selected from the group consisting of proteins, RNA and DNA from the lysed biological sample.

30. The method of claim 29, wherein the at least one class of biomolecules are RNA and/or DNA.

31. The method of claim 29, wherein step (5) comprises at least one chromatographic and/or solid phase-based purification or precipitation step.

32. The method of claim 31, wherein the at least one chromatographic and/or solid phase-based purification or precipitation step is selected from the group consisting of (a) gel filtration chromatography, (b) ion exchange chromatography, (c) reversed phase chromatography, and (d) precipitating and simultaneously binding the at least one class of biomolecules to a solid phase.

33. The method of claim 20, wherein the aqueous solution is an aqueous staining solution, comprising a dye or a substance that binds to a certain type of cell and/or cell component.

34. The method of claim 33, wherein the dye or the substance is selected from the group consisting of acridine dyes, anthraquinone dyes, arylmethane dyes, azo dyes, diazonium dyes, nitro dyes, phthalocyanine dyes, quinine imine dyes, tetrazolium dyes, thiazole dyes, xanthene dyes, hematoxylin, eosin, and mixtures thereof.

35. A kit for processing a wax-embedded biological sample, comprising:
   (1) a de-waxing agent that comprises a poly(organosiloxane) or a mixture of poly(organosiloxane)s,
   (2) an aqueous solution for partitioning a de-waxed sample and a liquefied embedding medium, wherein the aqueous solution is
      (a) an aqueous lysis buffer comprising a proteolytic agent, or
      (b) an aqueous staining solution comprising a dye or a substance that binds to a certain type of cell or cell component, and
   (3) a chromatographic device and/or a solid phase for isolating at least one class of biomolecules.

36. The kit of claim 35,
wherein the poly(organosiloxane)(s) is (are) poly(organosiloxane)s that
   a) has (have) a boiling point above 75° C., above 90° C., above 120 ° C., or above 140° C.,
   b) has (have) a kinematic viscosity of equal to or less than 5 mm$^2 \cdot$s$^{-1}$, equal to or less than 3 mm$^2 \cdot$s$^{-1}$, equal to or less than 2 mm$^2 \cdot$s$^{-1}$, or equal to or less than 1.5 mm$^2 \cdot$s$^{-1}$, and/or
   c) (i) is (are) selected from the group consisting of linear poly(organosiloxane)s,
      (ii) is (are) trialkylsiloxy-terminated polydialkylsiloxanes wherein "alkyl" comprises linear or branched $C_1$, $C_2$, $C_3$, $C_4$ $C_5$ or $C_6$ hydrocarbon chains,
      (iii) is (are) selected from the group consisting of linear trimethylsiloxy-terminated poly(dimethylsiloxane)s of the formula CH$_3$[Si(CH$_3$)$_2$O]$_n$Si(CH$_3$)$_3$, wherein the number of repeating units n is in the range of from 1 to 5, and/or
      (iv) is octamethyltrisiloxane (n=2).

37. The kit of claim 35, wherein the aqueous solution is an aqueous lysis buffer, and has one or more of the following features:
   a) the aqueous lysis buffer further comprises at least one buffering substance and a detergent,
   b) the proteolytic agent is a non-enzymatic proteolytic compound, and
   c) the proteolytic agent is a protease selected from the group consisting of proteinase K, trypsin, chymotrypsin, papain, pepsin, pronase, endoproteinase Lys-C, alpha-lytic proteinase, elastase, collagenase, bromocyane, recombinant *Bacillus* proteases, Lysozyme, and mixtures thereof.

38. The kit of claim 35, wherein the chromatographic device and/or solid phase is a chromatographic device and/or solid phase for carrying out a step selected from the group consisting of (a) gel filtration chromatography, (b) ion exchange chromatography, (c) reversed phase chromatography, and (d) precipitating and simultaneously binding the at least one class of biomolecules to the solid phase.

* * * * *